United States Patent
Pylant (10) Patent No.: US 11,010,810 B1
(45) Date of Patent: May 18, 2021

(54) COMPUTERIZED SYSTEM AND METHOD FOR AUTOMATICALLY ESTABLISHING A NETWORK CONNECTION FOR A REAL-TIME VIDEO CONFERENCE BETWEEN USERS

(71) Applicant: Brett Pylant, Grapevine, TX (US)

(72) Inventor: Brett Pylant, Grapevine, TX (US)

(*) Notice: Subject to any disclaimer, the term of this patent is extended or adjusted under 35 U.S.C. 154(b) by 310 days.

(21) Appl. No.: 15/594,332

(22) Filed: May 12, 2017

Related U.S. Application Data (60) Provisional application No. 62/335,405, filed on May 12, 2016.

(51) Int. Cl.
| | |
|---|---|
| *G06Q 30/00* | (2012.01) |
| *G06Q 30/06* | (2012.01) |
| *H04N 7/15* | (2006.01) |
| *G06F 16/78* | (2019.01) |
| *G06F 16/9535* | (2019.01) |
| *G06F 16/2457* | (2019.01) |
| *G06F 19/00* | (2018.01) |
| *G06Q 50/18* | (2012.01) |

(52) U.S. Cl.
CPC ... *G06Q 30/0627* (2013.01); *G06F 16/24578* (2019.01); *G06F 16/7867* (2019.01); *G06F 16/9535* (2019.01); *H04N 7/15* (2013.01); *G06F 19/3418* (2013.01); *G06Q 50/18* (2013.01)

(58) Field of Classification Search
CPC .................................................. G06Q 30/0627
See application file for complete search history.

(56) References Cited

U.S. PATENT DOCUMENTS

| | | | | |
|---|---|---|---|---|
| 2005/0159996 A1* | 7/2005 | Lazarus | ................. | G06Q 30/02 |
| | | | | 705/7.31 |
| 2016/0246936 A1* | 8/2016 | Kahn | ................. | G06Q 50/22 |
| 2017/0116679 A1* | 4/2017 | Abraham | ................. | G06Q 40/12 |
| 2017/0228525 A1* | 8/2017 | Wajs | ................. | G06F 21/36 |

OTHER PUBLICATIONS

Scott, Allan Mathieson. "Crime scene documentation." Wiley Encyclopedia of Forensic Science (2009).*

\* cited by examiner

*Primary Examiner* — Kathleen Palavecino
(74) *Attorney, Agent, or Firm* — Dickinson Wright PLLC; Kristopher Lance Anderson (57) ABSTRACT

Disclosed are systems and methods for improving interactions with and between computers in content generating, searching, hosting and/or providing systems supported by or configured with personal computing devices, servers and/or platforms. The systems interact to identify and retrieve data within or across platforms, which can be used to improve the quality of data used in processing interactions between or among processors in such systems. The disclosed systems and methods automatically, in real-time, establish a network connection between two users based on one user's current situation and the other user's determined expertise in that situation. The user's situation can be based on his/her identity, location, activity, the time, date, and the like. The disclosed systems and methods provide a computerized, fully automated network environment that enables video conferencing between such geographically separated users, thereby enabling the expert user to advise the other user on his/her current situation.

15 Claims, 5 Drawing Sheets

FIG. 5

COMPUTERIZED SYSTEM AND METHOD FOR AUTOMATICALLY ESTABLISHING A NETWORK CONNECTION FOR A REAL-TIME VIDEO CONFERENCE BETWEEN USERS

CROSS-REFERENCE TO RELATED APPLICATIONS

This application claims priority to U.S. Patent Appl. Ser. No. 62/331,896, filed May 4, 2016, entitled "Chemiluminescent System and Methods Related Thereto". The foregoing patent application is hereby incorporated herein by reference in its entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

STATEMENT REGARDING FEDERALLY SPONSORED RESEARCH OR DEVELOPMENT

None.

FIELD

The present disclosure relates generally to improving the performance of content generating, searching, providing and/or hosting computer systems and/or platforms by modifying the capabilities and providing non-native functionality to such systems and/or platforms for automatically establishing a network connection for video conferencing between a user and an expert user having an expertise associated with the determined specific and currently occurring real-world situation of the user.

SUMMARY

The present disclosure provides novel systems and methods for automatically, in real-time, establishing a network connection for video conferencing between a user and an expert user having an expertise associated with the determined specific and currently occurring real-world situation of the user. The disclosed systems and methods provide a user with the ability to interact with another user (e.g., expert user) in accordance with his/her current circumstances, such that the expert user the user is afforded the opportunity to interact with is identified based on the current circumstances of the user.

According to some embodiments, as discussed herein, the disclosed systems and methods provide a computerized, fully automated network environment that enables video conferencing between two geographically remote users. The two users are a first user that triggers a request for a second user, and the second user is an identified expert user that is identified and selected based on, inter alia, the circumstances of the first user, the credentials of the second user (and how that correlate to the first user's circumstances), the identity of the first user and/or second user, the activity of the first user, and the like, and/or some combination thereof.

Once second user (or expert user, used interchangeably herein) is identified, a video consultant session (or video conferencing session) is initiated between the two users. The session can be stored as it is occurring (e.g., in real-time as a media streaming event). In some embodiments, the storage of the session can occur locally on either or both users' device; and/or, in some embodiments, the video session can be stored on a server.

While the discussion herein will be directed to establishing a video conferencing session between two users, it should not be construed as limiting, as any interaction, whether iterative or in real-time can be established without departing from the scope of the instant disclosure. Indeed, communications occurring between a user and another user (e.g., second or expert user) can involve any type of internet provided and/or user generated content (UGC), including, but not limited to, images, video, text, audio, multimedia, RSS feeds, graphics interchange format (GIF) files, short-term videos (e.g., Vine® videos), and the like.

By way of a non-limiting example, user A is in situation X and he needs a consultant to assist him in situation X. User A initiates a request for a consultant. The disclosed systems and methods, as a result of the consultant request, can analyze the user's request to identify the situation's characteristics, analyze data associated with the user (e.g., the time, date, location of the user), and the like, or some combination thereof, in order to determine details (attributes, characteristics and/or descriptors) of the situation (e.g., situation X). This analyzed and identified information is then utilized to identify an expert user that has sufficient capabilities (e.g., a quantifiable amount of experience or credentials satisfying an expert level threshold) corresponding to the situation X. Once the expert user is identified, the expert user and the user A are automatically put in contact with one-another via a created/established network connection that includes a video conferencing session. From here, user A and the expert user can interact, and such interaction is stored for later retrieval and/or evidence. Additional features including recording of the session, storage of the session and the like may be further be implemented with the embodiments set forth herein.

In accordance with one or more embodiments, a method is disclosed for, inter alia, automatically establishing a network connection for video conferencing between a user and an expert user (consultant, doctor, attorney, representative) having an expertise associated with the determined specific and currently occurring real-world situation of the user.

In accordance with one or more embodiments, a non-transitory computer-readable storage medium is provided, the non-transitory computer-readable storage medium tangibly storing thereon, or having tangibly encoded thereon, computer readable instructions that when executed cause at least one processor to perform a method for automatically establishing a network connection for video conferencing between a user and an expert user having an expertise associated with the determined specific and currently occurring real-world situation of the user.

In accordance with one or more embodiments, a system is provided that comprises one or more computing devices configured to provide functionality in accordance with such embodiments. In accordance with one or more embodiments, functionality is embodied in steps of a method performed by at least one computing device. In accordance with one or more embodiments, program code (or program logic) executed by a processor(s) of a computing device to implement functionality in accordance with one or more such embodiments is embodied in, by and/or on a non-transitory computer-readable medium.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DESCRIPTION OF EMBODIMENTS

The present disclosure will now be described more fully hereinafter with reference to the accompanying drawings, which form a part hereof, and which show, by way of illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

For the purposes of this disclosure a computer readable medium (or computer-readable storage medium/media) stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a wired or wireless line or link, for example.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly.

A wireless network may further employ a plurality of network access technologies, including Wi-Fi, Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For purposes of this disclosure, a client (or consumer or user) device may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device an Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

A client device may vary in terms of capabilities or features. Claimed subject matter is intended to cover a wide range of potential variations. For example, a simple smart phone, phablet or tablet may include a numeric keypad or a display of limited functionality, such as a monochrome liquid crystal display (LCD) for displaying text. In contrast, however, as another example, a web-enabled client device may include a high resolution screen, one or more physical or virtual keyboards, mass storage, one or more accelerometers, one or more gyroscopes, global positioning system (GPS) or other location-identifying type capability, or a display with a high degree of functionality, such as a touch-sensitive color 2D or 3D display, for example.

A client device may include or may execute a variety of operating systems, including a personal computer operating system, such as a Windows, iOS or Linux, or a mobile operating system, such as iOS, Android, or Windows Mobile, or the like.

A client device may include or may execute a variety of possible applications, such as a client software application enabling communication with other devices, such as communicating one or more messages, such as via email, for example email, short message service (SMS), or multimedia message service (MMS), via a network, such as a social network or content delivery network, for example. A client device may also include or execute an application to communicate content, such as, for example, textual content, multimedia content, or the like. A client device may also include or execute an application to perform a variety of possible tasks, such as browsing, searching, playing or displaying various forms of content, including locally stored or streamed video, or games (such as fantasy sports leagues). The foregoing is provided to illustrate that claimed subject matter is intended to include a wide range of possible features or capabilities.

The principles described herein may be embodied in many different forms. The present disclosure provides novel systems and methods for automatically, in real-time, connecting two users based on one of the user's determined situation and the other user's determined expertise in such situation. That is, the disclosed systems and methods provide for automatically establishing a network connection for video conferencing between a user and an expert user having an expertise associated with the determined specific and currently occurring real-world situation of the user.

By way of background, currently, when a person is in a situation that requires immediate advice, the user must wait until the situation has concluded in order to receive said advice. For example, if user Jeff is pulled over for suspected drunken driving (e.g., DUI—driving under the influence), user Jeff would not have the ability to contact an attorney and receive legal advice until he is arrested and read his rights (e.g., Miranda Rights). This leaves a long period of time where Jeff, in the presence of law enforcement officials, is acting under his own, pedestrian, non-expert level understanding of the law. The disclosed system would enable Jeff, upon initiating a request, is able to reach, via preferably video, but at least via audio signal, an attorney to advise Jeff during his traffic stop. Jeff and his attorney would have previously formed an attorney-client relationship, via standard retainer for example. Therefore, the attorney is enabled via the disclosed system to remotely advise and advocate on behalf of client, Jeff.

The disclosed systems and method provide a fully automated, computerized mechanism that enables user's in similar situations to connect and interact with an expert (e.g., attorney, doctor and the like) that could properly assist them in their current situation.

By way of a non-limiting example, Jim is in a car accident and needs to talk to an attorney quickly and a doctor as well (as he is injured). Jim, via the disclosed systems and methods, initiates a consultant request for an attorney and doctor. As discussed herein, the request can comprise information associated with Jim's accident. For example, Jim has rear-ended another car (therefore he is technically at fault) and has broken his arm. This information can be included in the request(s) for the attorney and doctor.

In some embodiments, the request for the attorney and doctor can be included within a single request that an applicable server or program can decipher thereby leading to the proper expert discovery; and in some embodiments, two separate requests may be generated by Jim in order to identify the attorney and doctor respectively. While the discussion herein with focus on separate requests for individual expert users, it should not be construed as limiting, as a single request can comprise any amount of data, and additionally, any number of requests can be sent for any number of experts (e.g., 1 to n experts).

Turning to the attorney request, the request can include the location of Jim, and what transpired in the accident. Since the request if for an auto-accident, the request would result in identifying an attorney that typically handles such situations. After identifying the proper attorney, the attorney is sent a request for his/her availability, and should the attorney respond in the affirmative, Jim and the attorney are connected via a video conferencing session. Such session enables the attorney to provide legal advice to Jim on-the-spot, at the accident site.

In some embodiments, the video session is automatically recorded. As discussed below, such recording can be stored locally on either or both user's devices, or on a server for later retrieval. In some embodiments, the recording is augmented (or annotated) with data that indicates that the content of the recording is privileged. For example, when the expert is an attorney, doctor, psychiatrist or other professional that has a privilege that governs their communications, recorded content can be automatically augmented with data/metadata (e.g., tags) that indicate the content is protected.

According to some embodiments, the recording of the video can involve applying encryption to the video as it is occurring and/or being recorded. In some embodiments, the type of encryption algorithm or scheme applied may be selected and/or defined by a user, the system as a whole, an application or platform (e.g., video conferencing application or platform), and the like, or some combination thereof. According to some embodiments, any known or to be known negotiated encryption key or a pre-defined encryption key may be utilized by disclosed systems and methods without departing from the scope of the instant disclosure.

In some embodiments, if an attorney is not currently available, the disclosed systems and methods can trigger the automatic recording of the situation such that when an expert (e.g., attorney) is consulted, he/she can be provided the recording. For example, immediately upon the determination that an attorney is not available, Jim's mobile device can be automatically instructed to begin recording of the situation, such that the details of the accident, interactions with the police and the other participant in the accidence can be recorded for later analysis by the consulted attorney.

It should be understood that such recording capability is not based on whether the expert is an attorney, as such discussion above is based on an example embodiment; and, it should be understood that the automatic recording of a situation can occur based on any determination of an expert being unavailable (or temporarily unavailable—for example, if a video conferencing session is established, then is disconnected for a short time, recording can occur while the disconnection is occurring).

Turning to the doctor request, in a similar manner to the above attorney request, the request for the doctor can include the circumstances of the accident and the injuries (e.g., symptoms of Jim). In some embodiments, the request can include automatically detected biometrics input by Jim on his/her mobile device (e.g., any known or to be known biometric (e.g., finger-print, facial recognition) technology that can access and read a person's vitals. Based on such request, and since Jim has a broken arm, an orthopedic doctor can be identified. Once identified and determined to be available, a video conferencing session can be established between Jim and the doctor. Such interaction enables Jim to receive treatment (albeit, in some situations, preliminary treatment) that is not currently available.

Typically, such advice is unavailable, or not accessible in currently occurring real-world situations, as users typically must wait until the situation is over in order to receive advice/treatment from an expert; however, based on the novel, computerized systems and methods discussed herein, a user (e.g., Jim, for example) can have access to the requisite advice and/or treatment he/she is currently in need of.

Thus, the disclosed systems and methods provide the first fully automated network environment for a user an expert user to vide conference with each other based on the specific and currently occurring real-world situation of one (or both) of the users.

Figure 1:
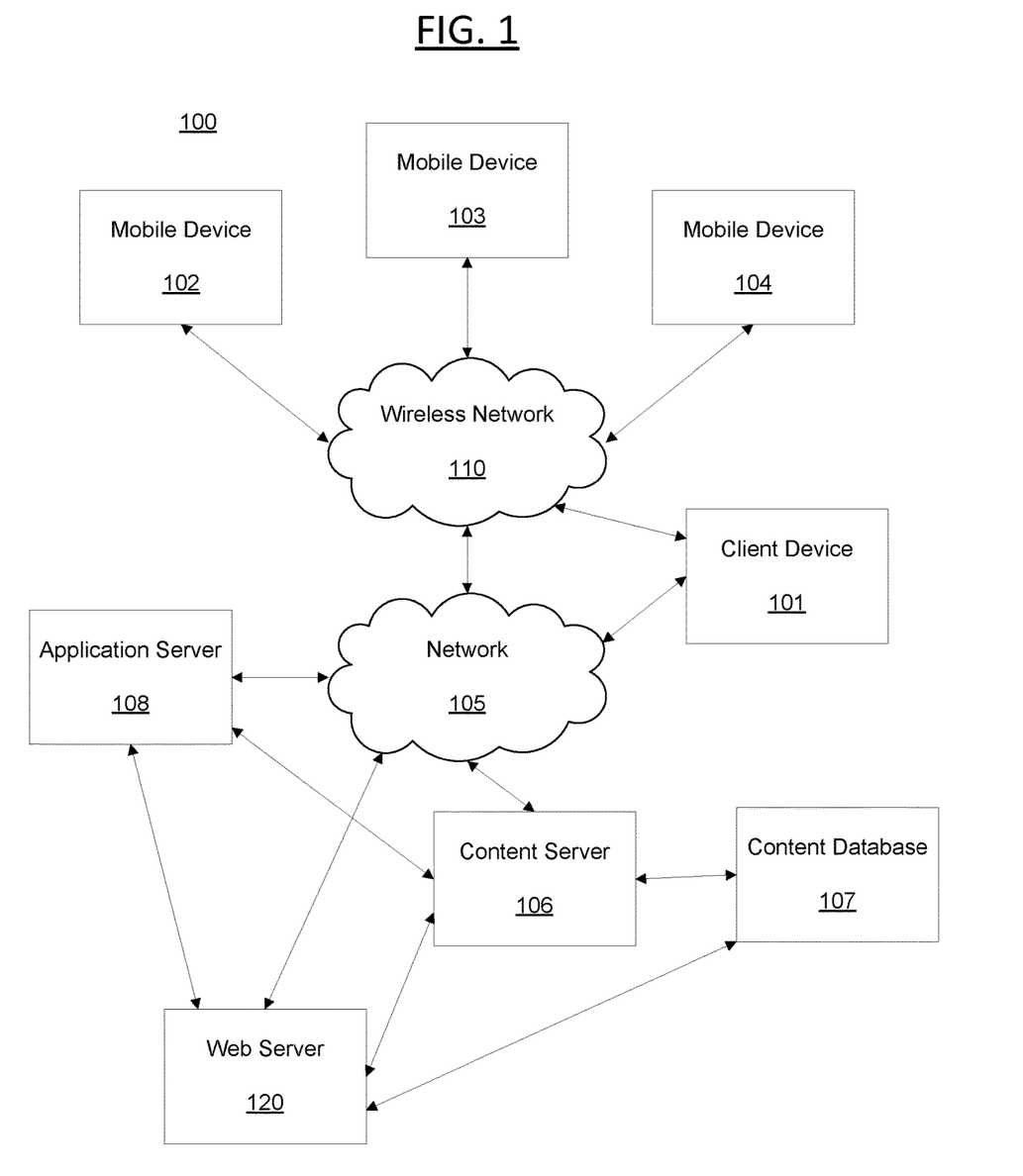
FIG. 1 is a schematic diagram illustrating an example of a network within which the systems and methods disclosed herein could be implemented according to some embodiments of the present disclosure.

Certain embodiments will now be described in greater detail with reference to the figures. In general, with reference to FIG. 1, a system 100 in accordance with an embodiment of the present disclosure is shown. FIG. 1 shows components of a general environment in which the systems and methods discussed herein may be practiced. Not all the components may be required to practice the disclosure, and variations in the arrangement and type of the components may be made without departing from the spirit or scope of the disclosure. As shown, system 100 of FIG. 1 includes local area networks ("LANs")/wide area networks ("WANs")-network 105, wireless network 110, mobile devices (client devices) 102-104 and client device 101. FIG. 1 additionally includes a variety of servers, such as content server 106, application (or "App") server 108, web server 120 and the like.

One embodiment of mobile devices 102-104 is described in more detail below. Generally, however, mobile devices 102-104 may include virtually any portable computing device capable of receiving and sending a message over a network, such as network 105, wireless network 110, or the like. Mobile devices 102-104 may also be described generally as client devices that are configured to be portable. Thus, mobile devices 102-104 may include virtually any portable computing device capable of connecting to another computing device and receiving information. Such devices include multi-touch and portable devices such as, cellular telephones, smart phones, display pagers, radio frequency (RF) devices, infrared (IR) devices, Personal Digital Assistants (PDAs), handheld computers, laptop computers, wearable computers, smart watch, tablet computers, phablets, integrated devices combining one or more of the preceding devices, and the like. As such, mobile devices 102-104 typically range widely in terms of capabilities and features. For example, a cell phone may have a numeric keypad and a few lines of monochrome LCD display on which only text may be displayed. In another example, a web-enabled mobile device may have a touch sensitive screen, a stylus, and an HD display in which both text and graphics may be displayed.

A web-enabled mobile device may include a browser application that is configured to receive and to send web pages, web-based messages, and the like. The browser application may be configured to receive and display graphics, text, multimedia, and the like, employing virtually any web based language, including a wireless application protocol messages (WAP), and the like. In one embodiment, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message.

Mobile devices 102-104 also may include at least one client application that is configured to receive content from another computing device. The client application may include a capability to provide and receive textual content, graphical content, audio content, and the like. The client application may further provide information that identifies itself, including a type, capability, name, and the like. In one embodiment, mobile devices 102-104 may uniquely identify themselves through any of a variety of mechanisms, including a phone number, Mobile Identification Number (MIN), an electronic serial number (ESN), or other mobile device identifier.

In some embodiments, mobile devices 102-104 may also communicate with non-mobile client devices, such as client device 101, or the like. In one embodiment, such communications may include sending and/or receiving messages, searching for, viewing and/or sharing photographs, audio clips, video clips, or any of a variety of other forms of communications. Client device 101 may include virtually any computing device capable of communicating over a network to send and receive information. The set of such devices may include devices that typically connect using a wired or wireless communications medium such as personal computers, multiprocessor systems, microprocessor-based or programmable consumer electronics, network PCs, or the like. Thus, client device 101 may also have differing capabilities for displaying navigable views of information.

Client devices 101-104 computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like.

Wireless network 110 is configured to couple mobile devices 102-104 and its components with network 105. Wireless network 110 may include any of a variety of wireless sub-networks that may further overlay stand-alone ad-hoc networks, and the like, to provide an infrastructure-oriented connection for mobile devices 102-104. Such sub-networks may include mesh networks, Wireless LAN (WLAN) networks, cellular networks, and the like.

Network 105 is configured to couple content server 106, application server 108, or the like, with other computing devices, including, client device 101, and through wireless network 110 to mobile devices 102-104. Network 105 is enabled to employ any form of computer readable media for communicating information from one electronic device to another. Also, network 105 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another, and/or other computing devices.

Within the communications networks utilized or understood to be applicable to the present disclosure, such networks will employ various protocols that are used for communication over the network. Signal packets communicated via a network, such as a network of participating digital communication networks, may be compatible with or compliant with one or more protocols. Signaling formats or protocols employed may include, for example, TCP/IP, UDP, QUIC (Quick UDP Internet Connection), DECnet, NetBEUI, IPX, APPLETALK™, or the like. Versions of the Internet Protocol (IP) may include IPv4 or IPv6. The Internet refers to a decentralized global network of networks. The Internet includes local area networks (LANs), wide area networks (WANs), wireless networks, or long haul public networks that, for example, allow signal packets to be communicated between LANs. Signal packets may be communicated between nodes of a network, such as, for example, to one or more sites employing a local network address. A signal packet may, for example, be communicated over the Internet from a user site via an access node coupled to the Internet. Likewise, a signal packet may be forwarded via network nodes to a target site coupled to the network via a network access node, for example. A signal packet communicated via the Internet may, for example, be routed via a path of gateways, servers, etc. that may route the signal packet in accordance with a target address and availability of a network path to the target address.

According to some embodiments, the present disclosure may also be utilized within or accessible to an electronic social networking site(s). A social network refers generally to an electronic network of individuals, such as acquaintances, friends, family, colleagues, or co-workers, which are coupled via a communications network or via a variety of sub-networks. Potentially, additional relationships may subsequently be formed as a result of social interaction via the communications network or sub-networks. In some embodiments, multi-modal communications may occur between members of the social network. Individuals within one or more social networks may interact or communication with other members of a social network via a variety of devices. Multi-modal communication technologies refers to a set of technologies that permit interoperable communication across multiple devices or platforms, such as cell phones, smart phones, tablet computing devices, phablets, personal computers, televisions, set-top boxes, SMS/MMS, email, instant messenger clients, forums, social networking sites, or the like.

In some embodiments, the disclosed networks 110 and/or 105 may comprise a content distribution network(s). A "content delivery network" or "content distribution network" (CDN) generally refers to a distributed content delivery system that comprises a collection of computers or computing devices linked by a network or networks. A CDN may employ software, systems, protocols or techniques to facilitate various services, such as storage, caching, communication of content, or streaming media or applications. A CDN may also enable an entity to operate or manage another's site infrastructure, in whole or in part.

The content server 106 may include a device that includes a configuration to provide content via a network to another device. A content server 106 may, for example, host a site or service, such as streaming media site/service, a gaming site, an email platform or social networking site, or a personal user site (such as a blog, vlog, online dating site, and the like). A content server 106 may also host a variety of other sites, including, but not limited to business sites, educational sites, dictionary sites, encyclopedia sites, wikis, financial sites, government sites, and the like. Devices that may operate as content server 106 include personal computers desktop computers, multiprocessor systems, microprocessor-based or programmable consumer electronics, network PCs, servers, and the like.

Content server 106 can further provide a variety of services that include, but are not limited to, streaming and/or downloading media services, search services, email services, photo services, web services, social networking services, news services, third-party services, audio services, video services, instant messaging (IM) services, SMS services, MMS services, FTP services, voice over IP (VOIP) services, or the like. Such services, for example a video application and/or video platform, can be provided via the application server 108, whereby a user is able to utilize such service upon the user being authenticated, verified or identified by the service. Examples of content may include images, text, audio, video, or the like, which may be processed in the form of physical signals, such as electrical signals, for example, or may be stored in memory, as physical states, for example.

In a similar manner as the discussed above in connection with the content server 106, the web server 120 can perform or have hosted therein, the same or similar capabilities. Indeed, the web server can be any type of server that can communicate information between and among users, such as, but not limited to, a social networking server, content distribution network server, instant messaging platform, video conferencing server, and the like.

Servers 106, 108 and 120 may be capable of sending or receiving signals, such as via a wired or wireless network, or may be capable of processing or storing signals, such as in memory as physical memory states. Devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally, a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

In some embodiments, users are able to access services provided by servers 106, 108 and/or 120. This may include in a non-limiting example, game servers, authentication servers, search servers, email servers, social networking services servers, SMS servers, IM servers, MMS servers, exchange servers, photo-sharing services servers, and travel services servers, via the network 105 using their various devices 101-104. In some embodiments, applications, such as a social networking application, photo-sharing/storage application, a streaming video application, blog, or gaming application, can be hosted by the application server 108 (or content server 106, web server 120 and the like). Thus, the application server 108 can store various types of applications and application related information including application data and user profile information (e.g., identifying and behavioral information associated with a user). It should also be understood that content server 106 can also store various types of data related to the content and services provided by content server 106 in an associated content database 107, as discussed in more detail below. Embodiments exist where the network 105 is also coupled with/connected to a Trusted Search Server (TSS) which can be utilized to render content in accordance with the embodiments discussed herein. Embodiments exist where the TSS functionality can be embodied within servers 106, 108 and/or 120.

Moreover, although FIG. 1 illustrates servers 106, 108 and 120 as single computing devices, respectively, the disclosure is not so limited. For example, one or more functions of servers 106, 108 and/or 120 may be distributed across one or more distinct computing devices. Moreover, in one embodiment, servers 106, 108 and/or 120 may be integrated into a single computing device, without departing from the scope of the present disclosure.

Figure 2:
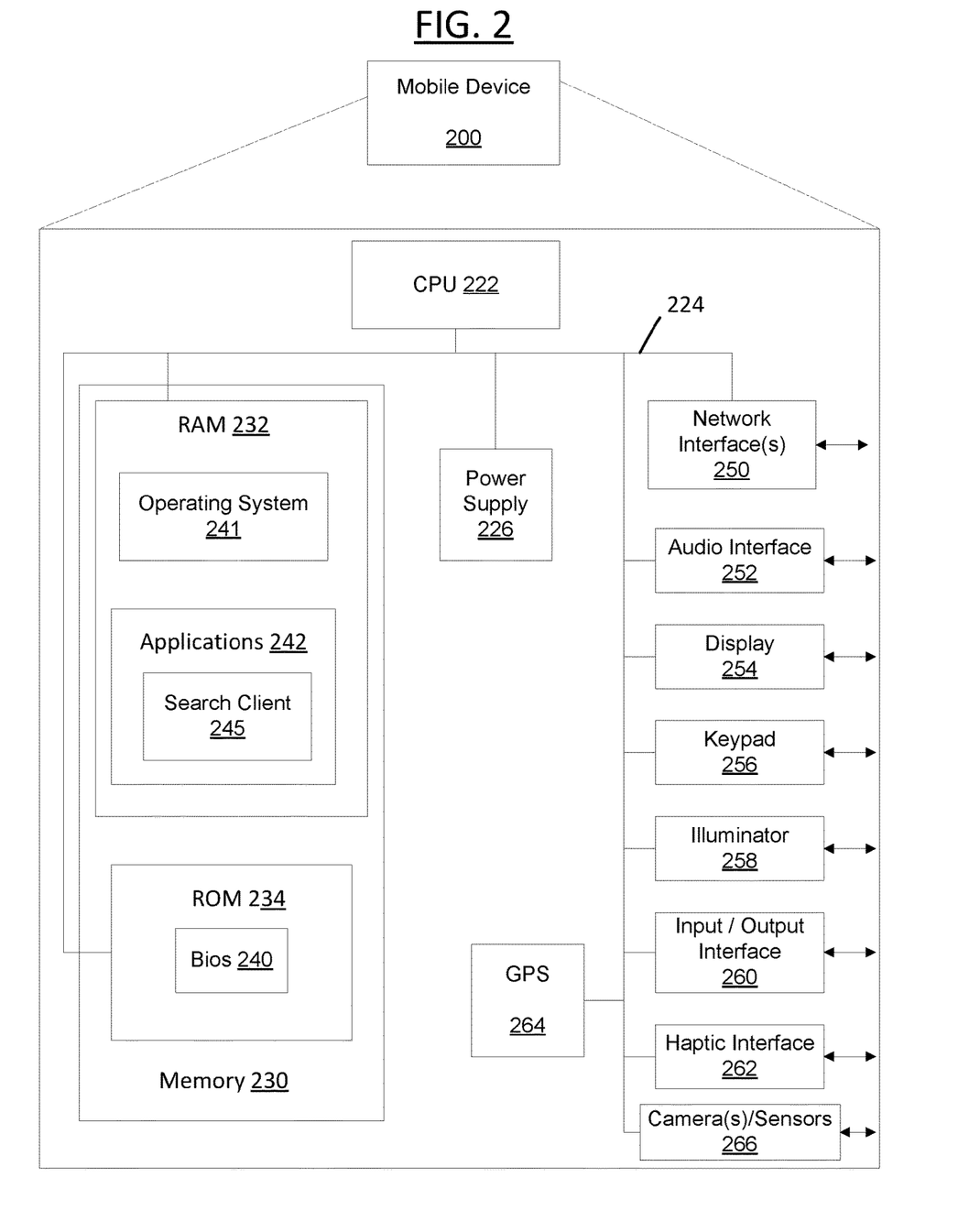
FIG. 2 depicts is a schematic diagram illustrating an example of client device in accordance with some embodiments of the present disclosure.

FIG. 2 is a schematic diagram illustrating a client device showing an example embodiment of a client device that may be used within the present disclosure. Client device 200 may include many more or less components than those shown in FIG. 2. However, the components shown are sufficient to disclose an illustrative embodiment for implementing the present disclosure. Client device 200 may represent, for example, client devices discussed above in relation to FIG. 1.

As shown in the figure, Client device 200 includes a processing unit (CPU) 222 in communication with a mass memory 230 via a bus 224. Client device 200 also includes a power supply 226, one or more network interfaces 250, an audio interface 252, a display 254, a keypad 256, an illuminator 258, an input/output interface 260, a haptic interface 262, an optional global positioning systems (GPS) receiver 264 and a camera(s) or other optical, thermal or electromagnetic sensors 266. Device 200 can include one camera/sensor 266, or a plurality of cameras/sensors 266, as understood by those of skill in the art. The positioning of the camera(s)/sensor(s) 266 on device 200 can change per device 200 model, per device 200 capabilities, and the like, or some combination thereof.

Power supply 226 provides power to Client device 200. A rechargeable or non-rechargeable battery may be used to provide power. The power may also be provided by an external power source, such as an AC adapter or a powered docking cradle that supplements and/or recharges a battery.

Client device 200 may optionally communicate with a base station (not shown), or directly with another computing device. Network interface 250 includes circuitry for coupling Client device 200 to one or more networks, and is constructed for use with one or more communication protocols and technologies as discussed above. Network interface 250 is sometimes known as a transceiver, transceiving device, or network interface card (NIC).

Audio interface 252 is arranged to produce and receive audio signals such as the sound of a human voice. For example, audio interface 252 may be coupled to a speaker and microphone (not shown) to enable telecommunication with others and/or generate an audio acknowledgement for some action. Display 254 may be a liquid crystal display (LCD), gas plasma, light emitting diode (LED), or any other type of display used with a computing device. Display 254 may also include a touch sensitive screen arranged to receive input from an object such as a stylus or a digit from a human hand.

Keypad 256 may comprise any input device arranged to receive input from a user. For example, keypad 256 may include a push button numeric dial, or a keyboard. Keypad 256 may also include command buttons that are associated with selecting and sending images. Illuminator 258 may provide a status indication and/or provide light. Illuminator 258 may remain active for specific periods of time or in response to events. For example, when illuminator 258 is active, it may backlight the buttons on keypad 256 and stay on while the client device is powered. Also, illuminator 258 may backlight these buttons in various patterns when particular actions are performed, such as dialing another client device. Illuminator 258 may also cause light sources positioned within a transparent or translucent case of the client device to illuminate in response to actions.

Client device 200 also comprises input/output interface 260 for communicating with external devices, such as a headset, or other input or output devices not shown in FIG. 2. Input/output interface 260 can utilize one or more communication technologies, such as USB, infrared, Bluetooth™, or the like. Haptic interface 262 is arranged to provide tactile feedback to a user of the client device. For example, the haptic interface may be employed to vibrate client device 200 in a particular way when the Client device 200 receives a communication from another user.

Optional GPS transceiver 264 can determine the physical coordinates of Client device 200 on the surface of the Earth, which typically outputs a location as latitude and longitude values. GPS transceiver 264 can also employ other geo-positioning mechanisms, including, but not limited to, tri-angulation, assisted GPS (AGPS), E-OTD, CI, SAI, ETA, BSS or the like, to further determine the physical location of Client device 200 on the surface of the Earth. It is understood that under different conditions, GPS transceiver 264 can determine a physical location within millimeters for Client device 200; and in other cases, the determined physical location may be less precise, such as within a meter or significantly greater distances. In one embodiment, however, Client device may through other components, provide other information that may be employed to determine a physical location of the device, including for example, a MAC address, Internet Protocol (IP) address, or the like.

Mass memory 230 includes a RAM 232, a ROM 234, and other storage means. Mass memory 230 illustrates another example of computer storage media for storage of information such as computer readable instructions, data structures, program modules or other data. Mass memory 230 stores a basic input/output system ("BIOS") 240 for controlling low-level operation of Client device 200. The mass memory also stores an operating system 241 for controlling the operation of Client device 200. It will be appreciated that this component may include a general purpose operating system such as a version of UNIX, or LINUX™, or a specialized client communication operating system such as Windows Client™, or the Symbian® operating system. The operating system may include, or interface with a Java virtual machine module that enables control of hardware components and/or operating system operations via Java application programs.

Memory 230 further includes one or more data stores, which can be utilized by Client device 200 to store, among other things, applications 242 and/or other data. For example, data stores may be employed to store information that describes various capabilities of Client device 200. The information may then be provided to another device based on any of a variety of events, including being sent as part of a header during a communication, sent upon request, or the like. At least a portion of the capability information may also be stored on a disk drive or other storage medium (not shown) within Client device 200.

Applications 242 may include computer executable instructions which, when executed by Client device 200, transmit, receive, and/or otherwise process audio, video, images, and enable telecommunication with a server and/or another user of another client device. Other examples of application programs or "apps" in some embodiments include browsers, calendars, contact managers, task managers, transcoders, photo management, database programs, word processing programs, security applications, spreadsheet programs, games, search programs, and so forth. Applications 242 may further include search client 245 that is configured to send, to receive, and/or to otherwise process a search query and/or search result using any known or to be known communication protocols. Although a single search client 245 is illustrated it should be clear that multiple search clients may be employed. For example, one search client may be configured to enter a search query message, where another search client manages search results, and yet another search client is configured to manage serving advertisements, IMs, emails, and other types of known messages, or the like.

Having described the components of the general architecture employed within the disclosed systems and methods, the components' general operation with respect to the disclosed systems and methods will now be described below.

Figure 3:
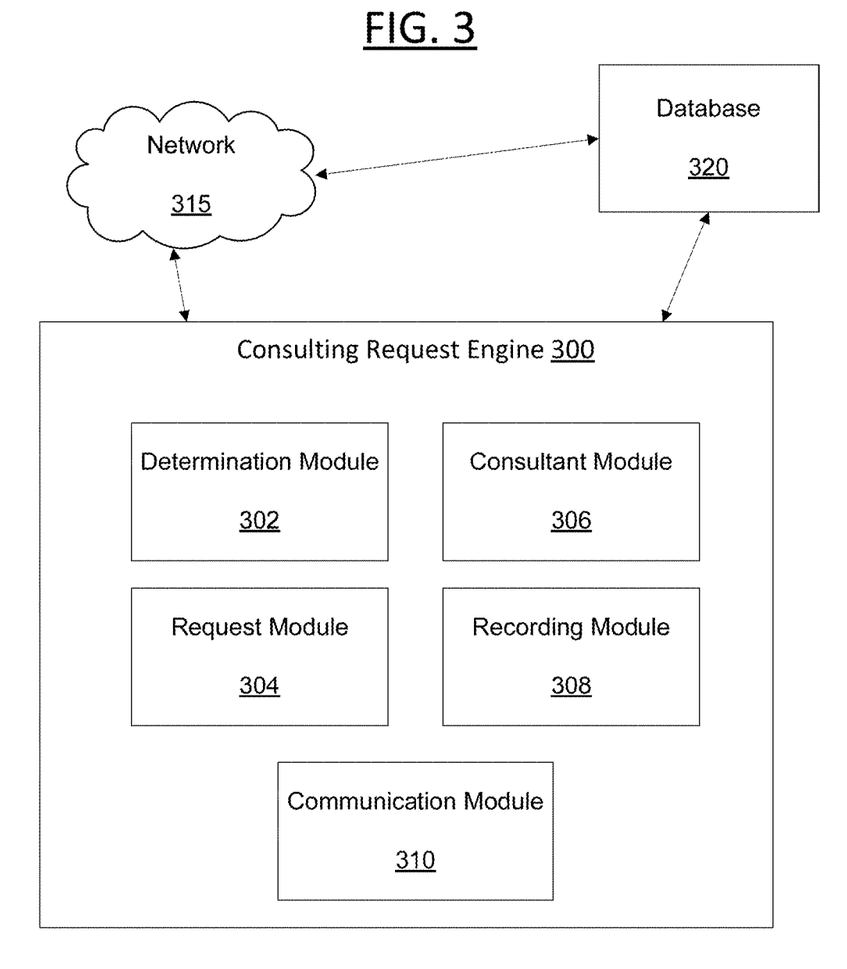
FIG. 3 is a schematic block diagram illustrating components of an exemplary system in accordance with embodiments of the present disclosure.

FIG. 3 is a block diagram illustrating the components for performing the systems and methods discussed herein. FIG. 3 includes a consulting request engine 300, network 315 and database 320. The consulting request engine 300 can be a special purpose machine or processor and could be hosted by an application server, content server, social networking server, web server, search server, content provider, email service provider, ad server, user's computing device, game server, and the like, or any combination thereof.

According to some embodiments, consulting request engine 300 can be embodied as a stand-alone application that executes on a user device. In some embodiments, the consulting request engine 300 can function as a downloadable application installed on the user's device, and in some embodiments, such application can be a web-based application accessed by the user device over a network. In some embodiments, the consulting request engine 300 can be installed as an augmenting script, program or application to another application, such as, for example, a video chat application (e.g., FaceTime®, Skype®, and the like) that enables two users to communicate in real-time via video conferencing.

The database 320 can be any type of database or memory, and can be associated with a content server on a network (e.g., content server 106, web server 120 or application server 108 from FIG. 1) or a user's device (e.g., device 101-104 or device 200 from FIGS. 1-2). Database 320 comprises a dataset of data and metadata associated with local and/or network information related to users, services, applications, content, and the like. Such information can be stored and indexed in the database 320 independently and/or as a linked or associated dataset. As discussed above, it should be understood that the data (and metadata) in the database 320 can be any type of information and type, whether known or to be known, without departing from the scope of the present disclosure.

According to some embodiments, database 320 can store data for users, e.g., user data. Such user data can be for those users requesting a consultant as well as user data for consultants.

According to some embodiments, the stored user data can include, but is not limited to, information associated with a user's profile, user interests, user's expertise and credentials, user's certifications, user behavioral information, user attributes, user preferences or settings, user demographic information, user location information, user biographic information, and the like, or some combination thereof. In some embodiments, the user data can also include, for purposes video conferencing, user device information, including, but not limited to, device identifying information, device capability information, voice/data carrier information, Internet Protocol (IP) address, applications installed or capable of being installed or executed on such device, and/or any, or some combination thereof. It should be understood that the data (and metadata) in the database 320 can be any type of information related to a user, content, a device, an application, a service provider, a content provider, whether known or to be known, without departing from the scope of the present disclosure.

According to some embodiments, database 320 can store data and metadata associated with media content (e.g., a recording of the video conference, as discussed below) from an assortment of media and/or service providers and/or platforms. For example, the information can be related to, but not limited to, content type of the media file, a category associated with the media, information associated with the application, provider or hosting entity of the media, information associated with the user requesting, storing and/or originating the media, and any other type of known or to be known attribute, characteristic, descriptor or feature associated with a media file.

According to some embodiments, as such media information is received, it can be stored in database 320 as an n-dimensional vector (or feature vector) representation for each media, where the information associated with the media can be translated as a node on the n-dimensional vector. Database 320 can store and index media information in database 320 as linked set of media data and metadata, where the data and metadata relationship can be stored as the n-dimensional vector. Such storage can be realized through any known or to be known vector or array storage, including but not limited to, a hash tree, queue, stack, VList, or any other type of known or to be known dynamic memory allocation technique or technology.

Indeed, in some embodiments, the user data stored in database 320 can also be stored as an n-dimensional vector in a similar manner as discussed in relation to the stored media. For example, a feature vector can be stored for each consultant user, and each node of the vector can correspond to information about the consultant (e.g., location, certifications, capabilities, skills, and the like).

While the storage discussion herein focuses on vector analysis, the stored information in database 320 can be analyzed, stored and indexed according to any known or to be known computational analysis technique or algorithm, such as, but not limited to, cluster analysis, data mining, Bayesian network analysis, Hidden Markov models, artificial neural network analysis, logical model and/or tree analysis, and the like.

As discussed above, with reference to FIG. 1, the network 315 can be any type of network such as, but not limited to, a wireless network, a local area network (LAN), wide area network (WAN), the Internet, or a combination thereof. The network 315 facilitates connectivity of the consulting request engine 300, and the database of stored resources 320. Indeed, as illustrated in FIG. 3, the consulting request engine 300 and database 320 can be directly connected by any known or to be known method of connecting and/or enabling communication between such devices and resources.

The principal processor, server, or combination of devices that comprises hardware programmed in accordance with the special purpose functions herein is referred to for convenience as consulting request engine 300, and includes a determination module 302, request module 304, consultant module 306, recording module 308 and communication module 310. It should be understood that the engine(s) and modules discussed herein are non-exhaustive, as additional or fewer engines and/or modules (or sub-modules) may be applicable to the embodiments of the disclosed systems and methods. The operations, configurations and functionalities of each module, and their role within embodiments of the present disclosure will be discussed with reference to FIGS. 3-4.

Figure 4:
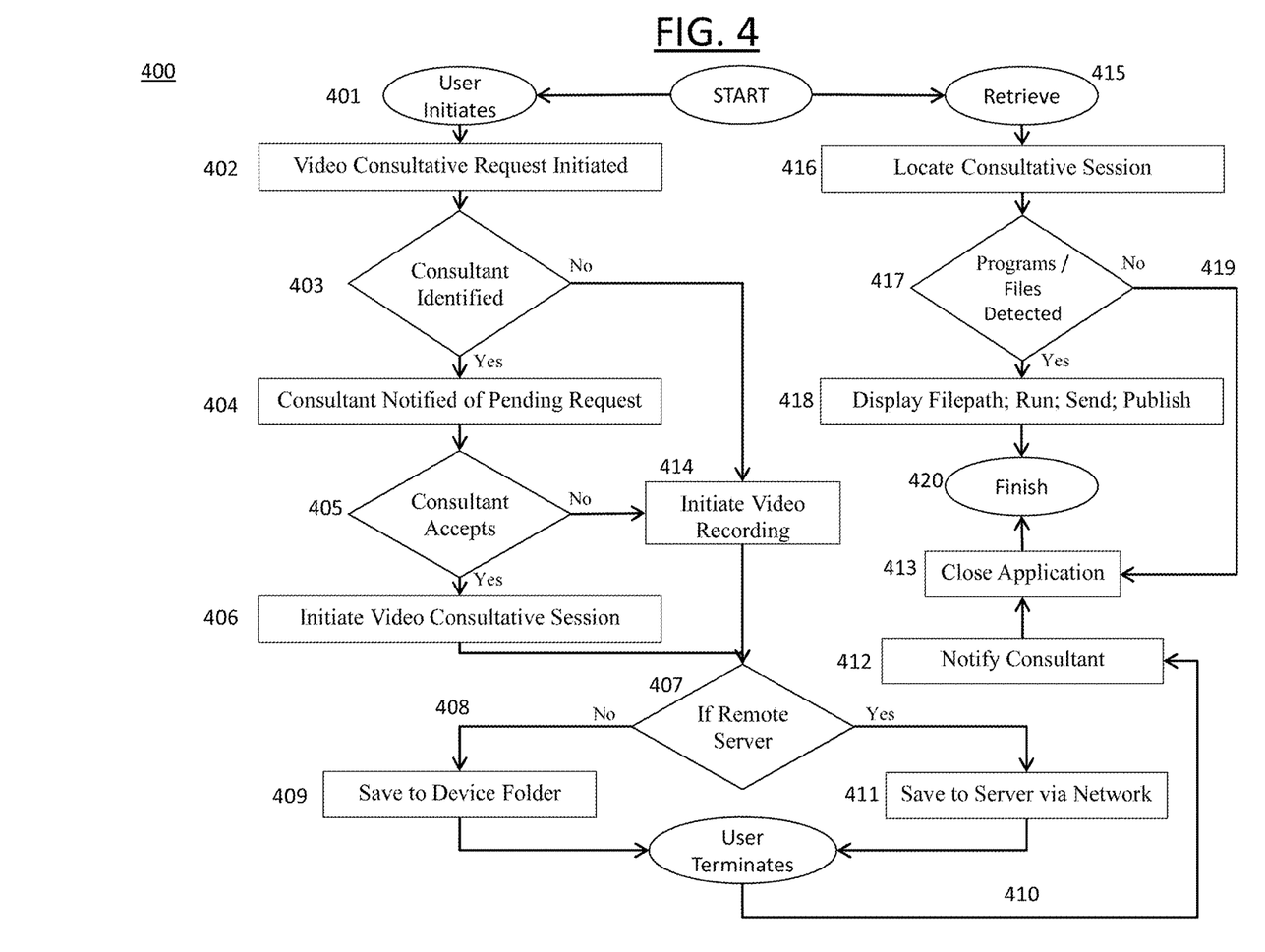
FIG. 4 is a flowchart illustrating steps performed in accordance with some embodiments of the present disclosure.

Turning to FIG. 4, Process 400 details some embodiments of automatically establishing a network connection for video conferencing between a user and an expert user having an expertise associated with the determined specific and currently occurring real-world situation of the user.

As discussed below, Steps 401 and 402 are performed by the determination module 302 of the consulting request engine 300, Steps 402 (along with the determination module 302) and 415-416 performed by the request module 304, Steps 403-405, 412 and 417 are performed by the consultant module 306, Steps 407-411 and 414 are performed by the recording module 308, and Steps 406, 413 and 418-420 are performed by the communication module 310.

In some embodiments, Process 400 begins with Step 401 where a user initiates the consulting request engine 300. As discussed above, such initiation can involve the determination of the current circumstances involving the initiating user (or a current context of the user). Such circumstances can include, but are not limited to, the activity of the user, identity of the user, the time, date, location, identity of other users involved in the activity, behavioral history of the user and/or other users involved in the activity, and the like, and/or some combination thereof.

In some embodiments, upon Step 401's initiation occurring, the determination module 302 can perform an accounting of the user's circumstances. Such accounting can involve identifying the data and/or metadata being collected and/or retrieved by the user's device in order to determine an activity, situation and/or circumstance of the user. As above, this accounting determination can provide the details surrounding user's current situation.

For example, the determination module 302 can detect via the GPS 264 unit on the user's device that the user is at a specific location. Additionally, analysis of the user's calendar and/or opened application shows that the user was at a party and is driving home (from the opened maps application executing on his/her device). This information can be utilized to determine which type of consultant/expert (used interchangeably herein) is being requested.

In some embodiments, the requirements for searching for an identifying an expert can be input by the user. For example, if the user is pulled over for speeding, the user can enter his location (to identify an attorney near that location or in that state) and which type of summons he is about to receive such that the appropriately skilled attorney can be identified.

In Step 402, a request for a consultant is compiled and communicated over a network in order to identify a consultant. The request triggers a search of database 320 in order to identify a consultant for the initiating user. In some embodiments, as discussed above, a request is created based on the circumstances surrounding imitating user. The request therefore can comprise information about a specific situation, information identifying the user, and the like. Such information can be automatically detected upon triggering a request initiation (as in Steps 401-402), and in some embodiments, such information can be entered by a user; and in some embodiments, the request information can be a combination of automatically detected and user entered information.

In Step 403, as a result of the communicated request from Step 402, a search is performed and determination is made regarding whether a consultant is identified from the request.

In some embodiments, the search can involve transforming the triggered request (from Step 402) into a feature vector, where the information associated with request can be translated into nodes on the vector (which is performed in a similar manner as discussed above). This vector is then used as a query to search the repository of vectors for consultants, as discussed above (see discussion of database 320 above). Once the vector(s) of a consultant(s) is identified, the consultant(s) associated with such vector(s) can be identified from the information in the vector(s).

In some embodiments, the search can involve a comparison of the request vector to the consultant vectors and identification of a consultant vector having the highest similarity to the request vector. In some embodiments, a set of consultants can be identified, where the consultant set can be associated with vectors being similar at or above a similarity threshold to the feature vector of the request. In such embodiments, the set of consultants can be ranked and the top ranked consultant can be identified, where the ranking is in accordance with an ordering of the similarity of the consultant vector to a request vector.

In some embodiments, the search can be based on a category of consultant. In such embodiments, the request vector is analyzed to determine a type of consultant being requested. This type information is determined by parsing the request vector and identifying the consultant type data in/on the vector. This type information/data is then used to filter the database 320 prior to the search so that only that type of consultant is identified.

In Step 404, if a consultant is identified (from Step 403), then the consultant is notified of a pending request. This notification can be any type of message or notification, including, but not limited to, an IM, SMS, MIMS, email, phone call, and the like. If the consultant accepts the request from Step 404, then a video conference session is initiated between the initiating user and the identified consultant. Step 406. In some embodiments, as discussed above, such session is recorded.

In Step 414, if either a consultant is not identified (from Step 403), or the consultant does not accept the request (from Step 405), then a recording is initiated, where such recording is performed by the device of the user respective to the scene of the user. As discussed above, the recording, whether of the conference session between the user and the consultant or of the scene by the user's device, can be stored in a remote server (e.g., on a network—Step 411), saved to a device folder (of the user and/or expert's device—Step 409). In some embodiments, a determination is made whether the remote server is available or accessible. Step 407. If it is, then the recording is saved to the server on a network (Step 411). If it is not (Step 408), then the recording is saved to the device folder of a user(s) device, and, in some embodiments, can be later uploaded to the server.

In Step 410, after the recording is concluded, or the session ends with the identified consultant, the consultant is notified of such termination (Step 412) and the consulting request engine (or application) is closed (Step 413). In other words, when communication between users over a created video conference session concludes, and/or recording of a scene by a user's device concludes, the application executing the video session (e.g., conference or scene recording) closes.

Continuing with Process 400, in some embodiments, Step 415 involves the retrieval of a recording, as discussed above. Step 416 involves a request for a retrieved recording, where the request and subsequent search performed in response to the request is performed in a similar manner as the search discussed above. The request can comprise information forming a search query that includes, but is not limited to, the date of a recording, the user's identity, consultant's identity, time of the recording, location where the recording occurred, location data associated with the content of the recording, and the like.

In Step 417, a determination is made whether there are programs or files associated with the requested recording. If yes, Step 418 retrieves the information associated with the recording. This information can include, but is not limited to, the file path (on the server or local device). Step 418's retrieval can also include retrieving the actual file from storage. In some embodiments, the retrieval can include identifying the recording and rendering it on a device of the retrieving user. In some embodiments, the retrieval can also include communicating (or publishing, sending or sharing) the recording to another user—for example, when the user retrieves the recording, he/she may want to send it to the consultant he/she spoke with). After retrieval (and communication, rendering and the like), the process ends. Step 420. In some embodiments, if the search results in no files being found, Step 419 involves closing the application, as in Step 413.

Figure 5:
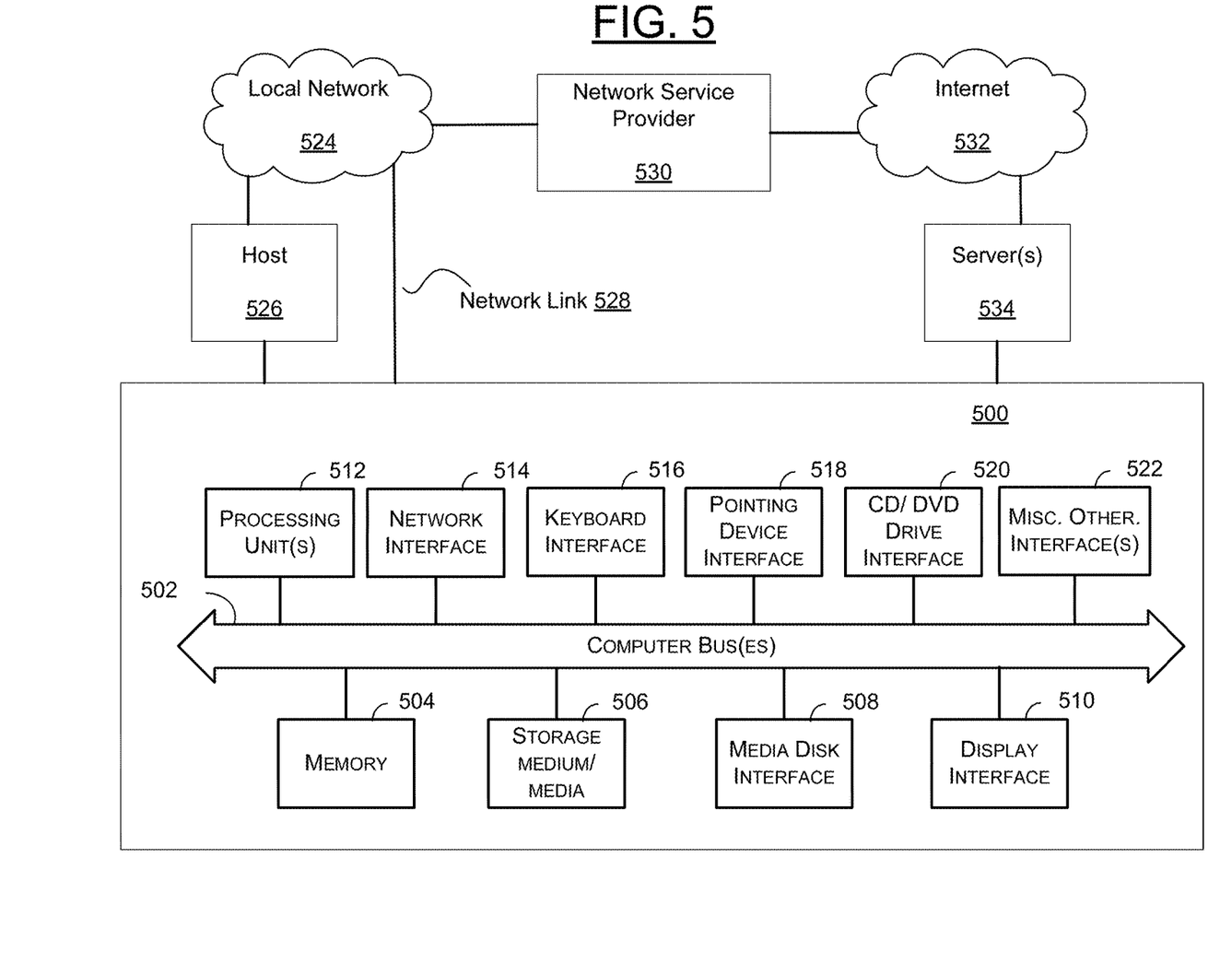
FIG. 5 is a block diagram illustrating the architecture of an exemplary hardware device in accordance with one or more embodiments of the present disclosure.

As shown in FIG. 5, internal architecture 500 of a computing device(s), computing system, computing platform, user devices, set-top box, smart TV and the like includes one or more processing units, processors, or processing cores, (also referred to herein as CPUs) 512, which interface with at least one computer bus 502. Also interfacing with computer bus 502 are computer-readable medium, or media, 506, network interface 514, memory 504, e.g., random access memory (RAM), run-time transient memory, read only memory (ROM), media disk drive interface 520 as an interface for a drive that can read and/or write to media including removable media such as floppy, CD-ROM, DVD, media, display interface 510 as interface for a monitor or other display device, keyboard interface 516 as interface for a keyboard, pointing device interface 518 as an interface for a mouse or other pointing device, and miscellaneous other interfaces not shown individually, such as parallel and serial port interfaces and a universal serial bus (USB) interface.

Memory 504 interfaces with computer bus 502 so as to provide information stored in memory 504 to CPU 512 during execution of software programs such as an operating system, application programs, device drivers, and software modules that comprise program code, and/or computer executable process steps, incorporating functionality described herein, e.g., one or more of process flows described herein. CPU 512 first loads computer executable process steps from storage, e.g., memory 504, computer readable storage medium/media 506, removable media drive, and/or other storage device. CPU 512 can then execute the stored process steps in order to execute the loaded computer-executable process steps. Stored data, e.g., data stored by a storage device, can be accessed by CPU 512 during the execution of computer-executable process steps.

Persistent storage, e.g., medium/media 506, can be used to store an operating system and one or more application programs. Persistent storage can also be used to store device drivers, such as one or more of a digital camera driver, monitor driver, printer driver, scanner driver, or other device drivers, web pages, content files, playlists and other files. Persistent storage can further include program modules and data files used to implement one or more embodiments of the present disclosure, e.g., listing selection module(s), targeting information collection module(s), and listing notification module(s), the functionality and use of which in the implementation of the present disclosure are discussed in detail herein.

Network link 528 typically provides information communication using transmission media through one or more networks to other devices that use or process the information. For example, network link 528 may provide a connection through local network 524 to a host computer 526 or to equipment operated by a Network or Internet Service Provider (ISP) 530. ISP equipment in turn provides data communication services through the public, worldwide packet-switching communication network of networks now commonly referred to as the Internet 532.

A computer called a server host 534 connected to the Internet 532 hosts a process that provides a service in response to information received over the Internet 532. For example, server host 534 hosts a process that provides information representing video data for presentation at display 510. It is contemplated that the components of system 500 can be deployed in various configurations within other computer systems, e.g., host and server.

At least some embodiments of the present disclosure are related to the use of computer system 500 for implementing some or all of the techniques described herein. According to one embodiment, those techniques are performed by computer system 500 in response to processing unit 512 executing one or more sequences of one or more processor instructions contained in memory 504. Such instructions, also called computer instructions, software and program code, may be read into memory 504 from another computer-readable medium 506 such as storage device or network link. Execution of the sequences of instructions contained in memory 504 causes processing unit 512 to perform one or more of the method steps described herein. In alternative embodiments, hardware, such as ASIC, may be used in place of or in combination with software. Thus, embodiments of the present disclosure are not limited to any specific combination of hardware and software, unless otherwise explicitly stated herein.

The signals transmitted over network link and other networks through communications interface, carry information to and from computer system 500. Computer system 500 can send and receive information, including program code, through the networks, among others, through network link and communications interface. In an example using the Internet, a server host transmits program code for a particular application, requested by a message sent from computer, through Internet, ISP equipment, local network and communications interface. The received code may be executed by processor 502 as it is received, or may be stored in memory 504 or in storage device or other non-volatile storage for later execution, or both.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

For the purposes of this disclosure the term "user", "subscriber" "consumer" or "customer" should be understood to refer to a user of an application or applications as described herein and/or a consumer of data supplied by a data provider. By way of example, and not limitation, the term "user" or "subscriber" can refer to a person who receives data provided by the data or service provider over the Internet in a browser session, or can refer to an automated software application which receives the data and stores or processes the data.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A method comprising steps of:
   determining, via a computing device, a context of a first user, said context corresponding to a current real-world situation of the first user;
   creating, via the computing device, a request for identification of a second user, said request comprising information associated with said current real-world situation of the first user;
   searching, via the computing device, a database comprising consultant information, said search comprising analyzing said consultant information and identifying a consultant that has associated consultant information corresponding to said context of the first user;
   communicating, via the computing device, a second request to said identified consultant, said second request comprising a notification that said first user requests consultation with said consultant;
   generating a request feature vector associated with said request;
   comparing said request feature vector to one or more consultant feature vectors associated with consultants stored in said database; and
   identifying a set of matched consultants having associated consultant feature vectors satisfying a similarity threshold when compared against said request feature vector further comprising determining, based on said search, a identified consultant that is available;
   upon determining that no identified consultant is available, causing a video recording of a scene associated with the current real-world situation;
   upon determining an identified consultant is available, automatically establishing, via the computing device over a network, a connection between the first user and the consultant, said connection comprising said computing device enabling a live video conference between said first user and the consultant;
   recording, via the computing device over the network, said live video conference; and
   retrieving, over the network, said recorded video conference; and rendering said recording.

2. The method of claim 1, wherein said context of the first user comprises at least one piece of context information selected from: a physical geographic location, a time, a date, an identity, and an activity.

3. The method of claim 1, wherein said consultant is identified in said set of matched consultants.

4. The method of claim 1, further comprising:
   ranking said set of matched consultants based on a similarity with the request, said similarity determined based upon said comparison; and
   identifying said identified consultant from said consultant set based on said ranking.

5. The method of claim 1, further comprising:
   determining a type of consultant required to satisfy said request, said determination comprising parsing said request in order to identify data within said real-world situation information that indicates said type; and
   filtering said database based on said type, wherein said search is based on said filtering.

6. The method of claim 1, wherein said recording further comprises storing said live video conference in said database.

7. The method of claim 1, wherein said recording further comprises storing said live video conference on a device of the first user or on a device of the consultant.

8. The method of claim 1, wherein said consultant determination is based on said identified consultant rejecting said second request.

9. The method of claim 1, wherein said recording further comprises annotating said recorded video conference with data indicating that the recording is protected.

10. A non-transitory computer-readable storage medium tangibly encoded with computer-executable instructions, that when executed by a processor associated with a computing device, performs a method comprising:
    determining a context of a first user, said context corresponding to a current real-world situation of the first user;
    creating a request for identification of a second user, said request comprising information associated with said current real-world situation of the first user;
    searching a database comprising consultant information, said search comprising analyzing said consultant information and identifying a consultant that has associated consultant information corresponding to said context of the first user;
    communicating a second request to said identified consultant, said second request comprising a notification that said first user requests consultation with said consultant;
    generating a request feature vector associated with said request;
    comparing said request feature vector to one or more consultant feature vectors associated with consultants stored in said database; and
    identifying a set of matched consultants having associated consultant feature vectors satisfying a similarity threshold when compared against said request feature vector further comprising determining, based on said search, a identified consultant that is available;
    upon determining that no identified consultant is available, causing a video recording of a scene associated with the current real-world situation;

upon determining an identified consultant is available, automatically establishing, over a network, a connection between the first user and the consultant, said connection comprising said computing device enabling a live video conference between said first and the consultant;

recording, over the network, said live videoconference; and retrieving, over the network, said recorded video conference; and rendering said recording.

11. The non-transitory computer-readable storage medium of claim 10, wherein said context of the first user comprises at least one piece of context information selected from: a physical geographic location, a time, a date, an identity, and an activity.

12. The non-transitory computer-readable storage medium of claim 10, further comprising: ranking said set of matched consultants based on a similarity with the request, said similarity determined based upon said comparison; and identifying said identified consultant from said consultant set based on said ranking.

13. The non-transitory computer-readable storage medium of claim 10, further comprising:
   determining a type of consultant required to satisfy said request, said determination comprising parsing said request in order to identify data within said real-world situation information that indicates said type; and
   filtering said database based on said type, wherein said search is based on said filtering.

14. The non-transitory computer-readable storage medium of claim 10, wherein said recording further comprises annotating said recorded video conference with data indicating that the recording is protected.

15. A computing device comprising:
   a processor;
   a non-transitory computer-readable storage medium for tangibly storing thereon program logic for execution by the processor, the program logic comprising:
      logic executed by the processor for determining a context of a first user, said context corresponding to a current real-world situation of the first user;
      logic executed by the processor for creating a request for identification of a second user, said request comprising information associated with said current real-world situation of the first user;
      logic executed by the processor for searching a database comprising consultant information, said search comprising analyzing said consultant information and identifying a consultant that has associated consultant information corresponding to said context of the first user;
      logic executed by the processor for communicating a second request to said identified consultant, said second request comprising a notification that said first user requests consultation with said consultant;
      logic executed by the processor for generating a request feature vector associated with said request;
      logic executed by the processor for comparing said request feature vector to one or more consultant feature vectors associated with consultants stored in said database; and
   logic executed by the processor for identifying a set of matched consultants having associated consultant feature vectors satisfying a similarity threshold when compared against said request feature vector further comprising determining, based on said search, a identified consultant that is available;
   logic executed by the processor for determining that, if no identified consultant is available, causing a video recording of a scene associated with the current real-world situation;
      logic executed by the processor that, upon determining an identified consultant is available automatically establishing, over a network, a connection between the first user and the consultant, said connection comprising said computing device enabling a live video conference between said first and the consultant;
      logic executed by the processor for recording, over the network, said live videoconference; and
      logic executed by the processor for retrieving, over the network, said recorded video conference; and rendering said recording.

\* \* \* \* \*